United States Patent
Pang et al.

(10) Patent No.: US 9,023,600 B2
(45) Date of Patent: May 5, 2015

(54) HIGHLY SELECTIVE PYROPHOSPHATE SENSOR

(75) Inventors: Yi Pang, Copley, OH (US); Weihua Chen, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/981,234

(22) PCT Filed: Feb. 16, 2012

(86) PCT No.: PCT/US2012/025380
§ 371 (c)(1),
(2), (4) Date: Jul. 23, 2013

(87) PCT Pub. No.: WO2013/109292
PCT Pub. Date: Jul. 25, 2013

(65) Prior Publication Data
US 2014/0004525 A1    Jan. 2, 2014

Related U.S. Application Data

(60) Provisional application No. 61/443,455, filed on Feb. 16, 2011.

(51) Int. Cl.
C12Q 1/68    (2006.01)
C12P 19/34    (2006.01)
(Continued)

(52) U.S. Cl.
CPC ............ *C12Q 1/6869* (2013.01); *A61K 31/315* (2013.01); *Y10T 436/16* (2015.01)

(58) Field of Classification Search
USPC .................. 435/6.1, 91.1; 548/100, 108
See application file for complete search history.

(56) References Cited

U.S. PATENT DOCUMENTS

2004/0220142 A1    11/2004 Marciani et al.
2005/0119497 A1    6/2005 Hong et al.
(Continued)

OTHER PUBLICATIONS

Chu et al., A fluorescent bis(benzoxazole) ligand: Toward binuclear Zn(II)-Zn(II) assembly, Dalton Trans., 2010, (published on the web May 4, 2010), vol. 39, pp. 5254-5259.
(Continued)

*Primary Examiner* — Jezia Riley
(74) *Attorney, Agent, or Firm* — Renner Kenner Greive Bobak Taylor & Weber (57) ABSTRACT

A dinuclear zinc complex PPi sensor is provided, that may be represented by the formula

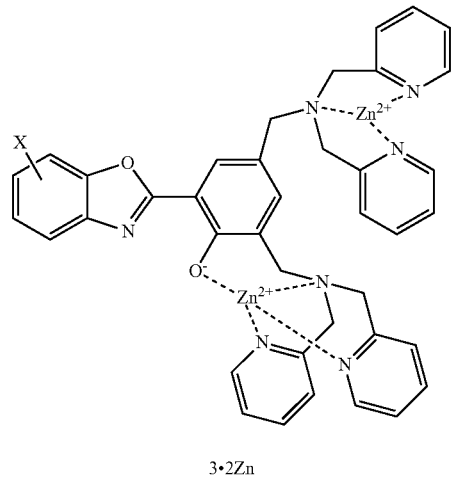

3·2Zn where X is hydrogen, —COOEt, —CH=$CH_2$, —OR, or —$NR_2$, wherein X is a monovalent organic group having from 1 to about 20 carbon atoms. A method of preparing the dinuclear zinc complex PPi sensor is also provided. Methods for detecting PPi in an aqueous solution and methods for pyrosequencing by using the dinuclear zinc complex are described.

10 Claims, 5 Drawing Sheets
(5 of 5 Drawing Sheet(s) Filed in Color)

(51) Int. Cl.
*C07D 293/00* (2006.01)
*C07F 3/12* (2006.01)
*A61K 31/315* (2006.01)

(56) References Cited

U.S. PATENT DOCUMENTS

2008/0020126 A1 1/2008 Arndt
2008/0261196 A1 10/2008 Yoon et al.
2009/0149341 A1 6/2009 Walt et al.

OTHER PUBLICATIONS

Lee et al., Quencher-fluorophore ensemble for detection of pyrophosphate in water. Tetrahedron Letters, 2007, vol. 48, pp. 4477-4480.

Kim et al., Excited State Intramolecular Proton Transfer and Charge Transfer Dynamics of a 2-(2'-Hydroxyphenyl) benzoxazole Derivative in Solution. J. Phys. Chem. A, 2010, vol. 114, pp. 5618-5629.

Chen et al., A Highly Selective Pyrophosphate Sensor Based on ESIPT Turn-On in Water, Org. Lett. Feb. 2011 (published on the Web Feb. 21, 2011), vol. 13(6), pp. 1362-1365.

HIGHLY SELECTIVE PYROPHOSPHATE SENSOR

RELATED APPLICATIONS

This application claims the benefit of U.S. Provisional Application No. 61/443,455, filed on Feb. 16, 2011, which is incorporated herein by reference.

TECHNICAL FIELD

The present invention relates to a highly selective sensor for pyrophosphate, wherein the sensing mechanism is based upon excited-state intramolecular proton transfer (ESIPT).

BACKGROUND OF THE INVENTION

The pyrophosphate ion may be represented by the chemical formula $P_2O_7^{2-}$, and is sometimes referred to by the abbreviation PPi.

PPi is a biologically significant anion which is involved in many cellular processes, such as cellular adenosine triphosphate (ATP) hydrolysis, DNA and RNA polymerizations, and enzymatic reactions. It has been reported that abnormal PPi levels can lead to vascular calcification resulting in severe medical conditions. The selective detection and quantification of PPi can provide insight into cellular processes and abnormalities.

Considerable efforts have been made to develop chemosensors for the optical detection of PPi. One of the early efforts in fluorescent sensing of PPi involved using a polyamine-attached anthracene derivative in 100% aqueous solution. However, poor sensitivity for PPi has hampered reliable fluorescent detection for PPi.

Pyrosequencing is a DNA sequencing technique that is based on a principle sometimes referred to as "sequencing by synthesis." Pyrosequencing utilizes enzyme-coupled reactions and bioluminescence to monitor the PPi release in real time. The method can be used for single-nucleotide polymorphism (SNP) analysis and tag sequencing (up to 100 bases), as well as for a whole-genome sequencing. The pyrosequencing technique relies on the enzymatic detection of the pyrophosphate that is released during a DNA polymerase chain reaction (PCR). The enzymatic reactions use two enzymes and two reagents (adenosine phosphosulfate (APS) and luciferin)), as shown in the following Scheme 1. The conversion of luciferin to oxyluciferin releases fluorescence at about 562 nanometers (nm). Luciferase controls the "on" and "off" of its bioluminescence, depending on the availability of ATP generated from PPi.

Scheme 1

The application requires the probe to specifically recognize the released PPi, in the presence of structurally similar anionic nucleotides. Enzymatic detection of PPi is a complicated scheme, and contributes to the high cost of DNA sequencing.

With the completion of human genome sequencing analysis, the genome-based medicine has come closer to reality. The high cost associated with the DNA sequencing remains to be an obstacle for achieving economically acceptable full-genome analysis in a clinical setting. Significant interest exists in searching for new methods and technologies that can sequence a human genome for $1,000 or less. Low-cost and faster ways to sequence DNA would revolutionize the use of genetic information and the nature of biological and biomedical research.

One significant challenge in the detection of PPi is the need to differentiate between structurally similar anions. Sensing systems for PPi that have improved sensitivity and selectivity, and are more cost effective are needed.

SUMMARY OF THE INVENTION

In at least one embodiment of the invention, a dinuclear zinc complex PPi sensor is provided that may be represented by the formula 3·2Zn where X is selected from the group consisting of hydrogen, —COOEt, —CH=CH₂, —OR, and —NR₂, where R is a monovalent organic group having from 1 to about 20 carbon atoms.

In yet another aspect of the invention, a method of preparing a dinuclear zinc complex PPi sensor is provided, the method comprising the steps of (1) reacting 2-(2'-hydroxyphenyl)-benzoxazole (HBO) or a derivative of HBO with 1-3 hexamethylenetetramine (HMTA) via a dual-Duff reaction, to form a dialdehyde intermediate that may be represented by the formula

6 wherein X is selected from the group consisting of hydrogen, —COOEt, —CH=CH₂, —OR, and —NR₂, then (2) combining the dialdehyde, sodium triacetoxyborohydride [NaBH(OAc)₃], and a bis(2-pyridylmethyl)amino compound in a reductive amination reaction, to form a compound containing two bis(2-pyridylmethyl)amino groups, said compound being represented by the formula

3 then (3) combining the product of the reductive amination reaction with zinc nitrate Zn(NO₃)₂ to form a dinuclear Zn²⁺ complex, that may be represented by the formula 3·2Zn wherein one of the Zn²⁺ cations is bonded to a phenol oxygen, removing the phenolic proton and turning off the luminescence from the excited state intramolecular proton transfer (ESIPT).

In a further aspect of the invention, a method of detecting PPi in an aqueous solution is provided, the method comprising the steps of providing an aqueous solution containing a di-nuclear Zn complex PPi sensor that can react immediately with PPi to detect PPi's presence, wherein the structure of the PPi sensor may be represented by the formula 3·2Zn wherein X is selected from the group consisting of hydrogen, —COOEt, —CH=CH₂, —OR, and —NR₂, and wherein any PPi present in the aqueous solution will combine with said dinuclear Zn complex, thereby creating a measurable fluorescent signal.

In another aspect of the invention, a method of pyrosequencing is provided, the method comprising the steps of (1) providing a DNA template having a base at a target position and an extension primer; (2) subjecting the DNA template and extension primer to a polymerase reaction in the presence of (a) a deoxynucleotide or dideoxynucleotide, and (b) a dinuclear zinc complex PPi sensor represented by the formula 3·2Zn where X is selected from the group consisting of hydrogen, —COOEt, —CH=CH₂, —OR, and —NR₂, wherein said nucleotide will become incorporated onto the DNA template and release PPi if the nucleotide is complementary to the base in the target position, and wherein said released PPi combines with said dinuclear zinc complex and a new fluorescent emission is produced.

In one or more embodiments of the above methods, a large fluorescent bathochromic shift of at least about 100 nm is generated.

In one or more embodiments of the above methods, the new emission is produced with peak $\lambda_{em}$=518 nm.

In one or more embodiments of the above method of pyrosequencing, different deoxynucleotides or dideoxynucleotides are added either to separate aliquots of DNA-primer mixture or successively to the same DNA-primer mixture and subjected to the polymerase reaction to indicate whether the nucleotide is incorporated.

One or more embodiments of the above method of pyrosequencing may take place in aqueous droplets in an oil phase (emulsion PCR).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Advantages of the present invention will become better understood with regard to the following description, appended claims, and accompanying drawings wherein:

DETAILED DESCRIPTION OF ILLUSTRATIVE EMBODIMENTS

The present invention provides a ratiometric fluorescent sensor mechanism for PPi detection. In one or more embodiments, the sensor facilitates selective qualitative and/or quantitative detection of PPi in aqueous systems. In one or more embodiments, the mechanism integrates a reliable chemical event in the sensor, that can be triggered upon PPi binding to generate a large fluorescence response. In one or more embodiments, the ratiometric fluorescent sensor mechanism utilizes excited state intramolecular proton transfer (ESIPT) to trigger a fluorescence response.

Conventional systems have utilized a binuclear metal complex in conjunction with bis(2-pyridylmethyl)amine (DPA) ligands as shown in Scheme 2.

An example of 1, where R is —N═N—Ar, has been used, wherein the selective binding of PPi produces the non-fluorescent structure 2, and shows a color response ($\lambda_{max}$ red shift by about 48 nanometers (nm)). The use of a fluorescein derivative has resulted in a relatively small (about 11 nm) red shift in fluorescence signal. The use of a coumarin derivative has also resulted in a relatively small (about 20 nm) red shift in fluorescence signal. These systems lack large signal responses and selectivity to PPi, which are necessary for practical application of PPi sensor.

In contrast, the sensor system of the present invention is based on intramolecular hydrogen bonding in 2-(2-hydroxyphenyl)-1,3-benzoxazole (HBO) derivatives, which exhibit excited state intramolecular proton transfer (ESIPT) to give a large Stokes shift (100-200 nm). Sensor 3.2Zn may be employed as a PPi sensor, wherein ESIPT is used as a switching mechanism in a buffered aqueous solution. Briefly, the phenoxide "oxygen" of the sensor 3.2Zn chelates a $Zn^{2+}$ center to disable ESIPT. Analyte recognition is possible when PPi simultaneously connect to two $Zn^{2+}$ centers in 4, as shown in Scheme 3, which moves the $Zn^{2+}$ away to free the phenol moiety for ESIPT. The well-defined chemical event in the molecular design leads to a highly selective probe for PPi, with fluorescence changing from blue to green (corresponding to the bathochromic shift of ~100 nm, FIG. 1). This is illustrated in Scheme 3; where X is a moiety that may be selected to further shift the fluorescence signal toward longer wavelengths.

Scheme 3

In one or more embodiments, sensor 3.2Zn may be synthesized according to the reaction shown in Scheme 4. The sensor 3.2Zn may be synthesized from a hydroxyphenyl benzoxazole such as 2-(2'-hydroxyphenyl)benzoxazole (HBO) 5, or a derivative thereof. Dialdehyde intermediate 6 may be obtained by a dual-Duff reaction. The dialdehyde intermediate 6 may be further transformed into 3 by a reductive amination to install the two bis(2-pyridylmethyl)amino groups. The dinuclear $Zn^{2+}$ complex 3.2Zn may be formed by the addition of a methanolic solution of 3 to an aqueous solution of 2.0 equiv of $Zn(NO_3)_2$. In one or more embodiments, the overall yield is 55% from 5. For comparison, a mono-nuclear $Zn^{2+}$ complex 8.Zn may be synthesized in a similar route, and in one or more embodiments achieve an overall yield of 49% from 2-hydroxy-5-methylbenzaldehyde 7.

Scheme 4

In one or more embodiments, the aqueous sensor solution may be further diluted with water as desired. In one or more embodiments, the aqueous sensor solution further comprises a buffer. Suitable buffers include Good's buffers. In one or more embodiments, the buffer is selected from 2-(N-morpholino)ethanesulfonic acid (MES), N-(carbamoylmethyl)iminodiacetic acid (ADA), piperazine-N,N'-bis(2-ethanesulfonic acid (PIPES), N-(2-Acetamido)-2- aminoethanesulfonic acid (ACES), Cholamine chloride, BES, 2-[[1,3-dihydroxy-2-(hydroxymethyl)propan-2-yl]amino]ethanesulfonic acid (TES), 4-(2-hydroxyethyl)-1-piperazineethanesulfonic acid (HEPES), Acetamidoglycine, Tricine, Glycinamide, and Bicine. In one or more embodiments, the buffer is HEPES.

In one or more embodiments, the pH of the buffered sensor solution is about 7.4.

Advantageously, the sensor system of the present invention can detect PPi in a single step, thereby greatly simplifying the enzymatic detection scheme.

In order to demonstrate the practice of the present invention, the following examples have been prepared and tested. The examples should not, however, be viewed as limiting the scope of the invention. The claims will serve to define the invention.

Scheme 5

ESIPT masked
9

10

In one or more embodiments, ESIPT turn-on in 3.2Zn requires the analyte, such as PPi, to simultaneously bind to two $Zn^{2+}$ sites. Interaction of 3.2Zn with PPi anion initially leads to a complex that may be represented by formula 9 of Scheme 5 above, wherein an oxygen attached to a first phosphorus atom of PPi binds with a first $Zn^{2+}$ center ($Zn_1$, at the top of 9), and then an oxygen attached to the second phosphorus atom of PPi binds with the second $Zn^{2+}$ center ($Zn_2$, at the bottom of 9), thereby forming the structure that may be represented by formula 10 above.

Figure 5:
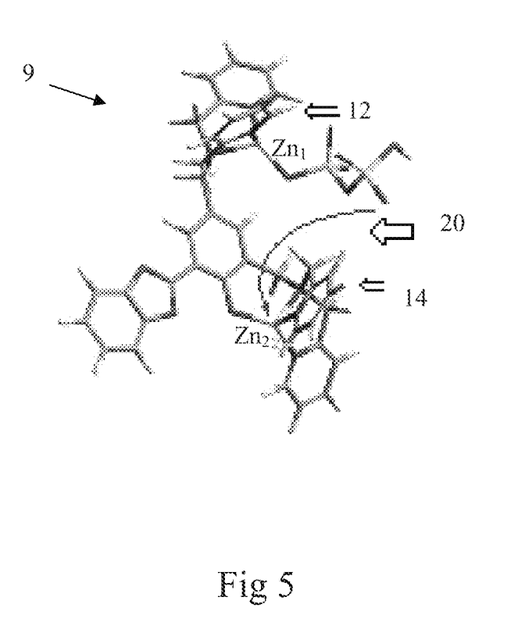
FIG. 5 is a molecular model representation

Molecular modeling of the structure shown in FIG. 5 for formula 9 indicates that the first $Zn^{2+}$ center, generally denoted $Zn_1$ and the second $Zn^{2+}$ center, generally denoted $Zn_2$, are separated by about 7.35 Å, which is beyond the distance a mono anion such as $HCO_3^{2-}$ and $H_2PO_4^-$ can bridge. A first pyridyl ring (vertical) is indicated by 12. A second pyridyl ring (vertical) is indicated by 14. An area of possible steric interaction is generally indicated by 20. Advantageously, the pyridyl ring at $Zn_2$ can act as a gate to allow the less hindered phosphate anion to pass. In contrast, the bulky tail of ATP would have increased steric interaction with the pyridyl ring at the gate, and the associated phosphate anion would be prevented from entering into the cavity to bind to $Zn_2$. Thus, it is believed that the unique steric interaction posed by the pyridylmethyl group plays an important role in the sensor ability to differentiate PPi from the structural analogue ATP.

EXAMPLES

Example 1

The sensor 3.2Zn was synthesized according to the reaction shown in Scheme 4. More specifically, 3.2Zn was synthesized from a hydroxyphenyl benzoxazole such as 2-(2'-hydroxyphenyl)benzoxazole (HBO) 5. Dialdehyde intermediate 6 was obtained by a dual-Duff reaction. The dialdehyde intermediate 6 was further transformed into 3 by a reductive amination to install the two bis(2-pyridylmethyl) amino groups. The dinuclear $Zn^{2+}$ complex 3.2Zn was formed by the addition of a methanolic solution of 3 to an aqueous solution of 2.0 equiv of $Zn(NO_3)_2$. The overall yield is 55% from 5.

Figure 1A:
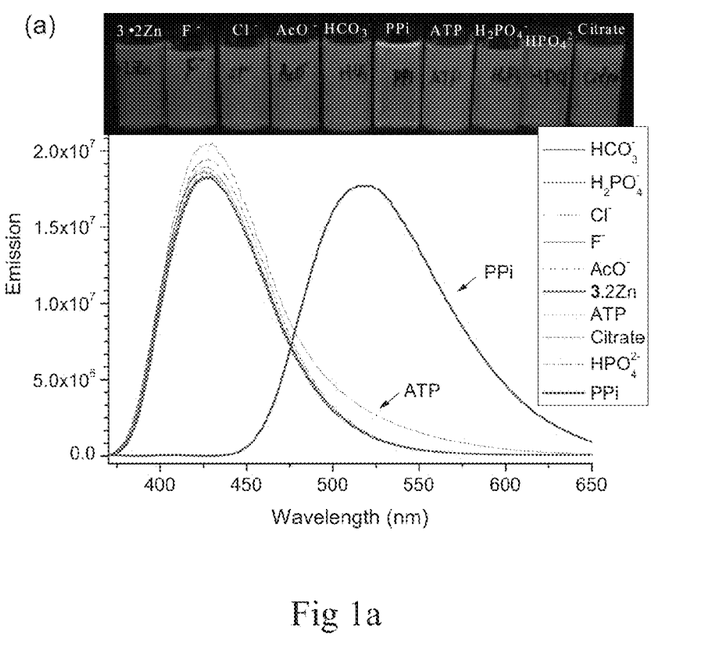
FIGS. 1(a) and 1(b) are fluorescence spectra as described herein.

FL spectra of sensor 3.2Zn (12 μM) in aqueous solution of 10 mM HEPES buffer (pH 7.4) at 25° C. in the presence of various anions (600 μM), and their fluorescent images when irradiated at 365 nm, are shown in FIG. 1(*a*).

Figure 1B:
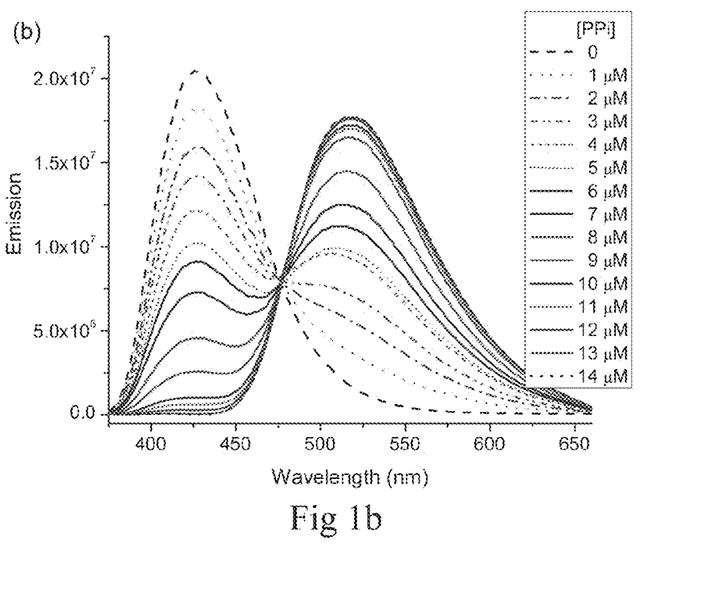

The change in fluorescence emission of 3.2Zn (12 μM) upon addition of PPi (the sodium salt) in an aqueous solution of 10 mM HEPES buffer (pH 7.4) at 25° C. is shown in FIG. 1(*b*).

FIG. 1 shows the effect of anions (sodium salts) on the fluorescence spectrum of 3.2Zn in a buffered aqueous solution (pH=7.4). In the absence of an anion guest, sensor 3.2Zn gives emission at 420 nm. This fluorescent emission was not changed upon addition of excessive $HPO_4^{2-}$, $CH_3CO_2^-$, citrate ion, etc. In contrast, PPi anion caused the emission band to be shifted to a longer wavelength (at 518 nm). The large bathochromic shift (~100 nm) in emission is attributed to the keto emission arising from ESIPT.

Although the related phosphate analogues ATP slightly increased the fluorescence intensity, its binding with 3.2Zn was not sufficiently strong to enable the ESIPT. Job's plot revealed that the complex had a 1:1 stoichiometry for 3.2Zn and PPi. The formation of a 1:1 complex was further supported by electrospray mass spectrometry (ES-MS) data, which detected the complex at m/z=936 corresponding to $[C_{39}H_{36}N_7O_9P_2Zn_2]+(=[3.2Zn+PPi+H^+]^+)$ and a peak at m/z=934 corresponding to the deprotonated phenoxide, $[C_{39}H_{35}N_7O_9P_2Zn_2]-(=[3.2Zn+PPi-H^+]^-)$.

Figure 2:
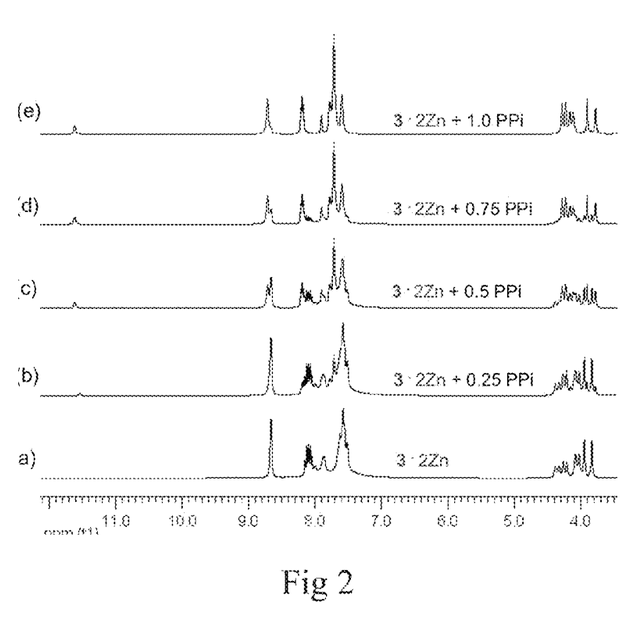
FIG. 2 is an $^1$H NMR spectra as described herein.
Figure 3:
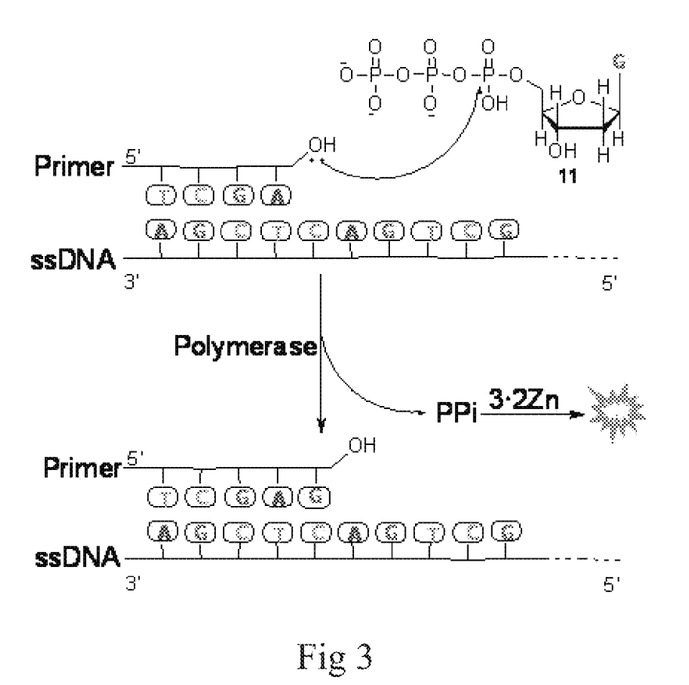
FIG. 3 is a schematic representation of a mechanism of sensing PPi released from PCR according to one embodiment of the present invention.

$^1$H NMR spectra is shown in FIG. 2 for 3.2Zn (1.5 mM) with various molar ratio of hydrogen pyrophosphate ($Na_3HP_2O_7$, HPPi) in DMSO-d.

The four pKas of pyrophosphoric acid ($H_4P_2O_7$) have been reported to be 0.9, 2.0, 6.6, and 9.4. At pH 7.4, an aqueous solution of pyrophosphoric acid consists of 85.6% $HA^{3-}$, 13.6% $H_2A^{2-}$ and 0.7% $A^{4-}$. The chemical shift of the intramolecular H-bonding in the HBO system is typically around 11 ppm. Upon titration of 3.2Zn with hydrogen pyrophosphate, the $^1$H NMR spectra (FIG. 2) revealed a new peak at 11.6 ppm corresponding to the intramolecular H-bonding between the phenolic proton and benzoxazole nitrogen. The intensity of this peak increased with the amount of HPPi. The result indicated that the phenoxide oxygen was released from the metal-binding by the cooperative coordination of PPi with the two $Zn^{2+}$ ions, which supports the proposed PPi sensing mechanism shown in Scheme 3.

Comparative Example 2 a mono-nuclear $Zn^{2+}$ complex 8.Zn was synthesized in a similar route in an overall yield of 49% from 2-hydroxy-5-methylbenzaldehyde 7, as shown in Scheme 4 above.

Mononuclear 8.Zn was titrated with PPi under the same conditions as for dinuclear 3.2Zn above. Addition of PPi increased the fluorescence intensity at 427 nm without inducing a notable bathochromic shift. The result indicated that no ESIPT was induced from 8.Zn complex. In other words, PPi was bound to the $Zn^{2+}$ in the mononuclear complex without breaking the existing Zn—O bond.

From the fluorescence titration experiments, the association constant of 3.2Zn with PPi and 8.Zn with PPi were calculated to be $9.2 \times 10^7$ $M^{-1}$ and $1.8 \times 10^4$ $M^{-1}$ respectively. Association constants were obtained by a global non-linear least-squares fit of the data with the program Specfit/32, available from Spectrum Software Associates, Marlborough, Mass. It therefore can be concluded that the ESIPT turn-on in 3.2Zn required the analyte to simultaneously bind to two $Zn^{2+}$ sites. It was assumed that interaction of 3.2Zn with PPi anion initially led to 9 (Scheme 5). The negative charged oxygen at the other end of PPi then reached out to the second $Zn^{2+}$ site to form 10. Molecular modeling of 9 showed that the $Zn_1$ and $Zn_2$ centers were separated by 7.35 Å, which was beyond the distance a mono anion such as $HCO_3^{2-}$ and $H_2PO_4^{-1}$ can bridge. As seen from the model of 9, the pyridyl ring at the second zinc center (labeled $Zn_2$) acted as a gate to allow the less hindered phosphate anion to pass. In contrast, the bulky tail of ATP would have increased steric interaction with the pyridyl ring at the gate, which prevents the associated phosphate anion from entering into the cavity to bind to the second $Zn^{2+}$ site. In other words, the unique steric interaction posed by the pyridylmethyl group plays an important role in the sensor ability to differentiate PPi from the structural analogue ATP.

In order to demonstrate the applicability of the invention sensor of pyrosequencing, sensor 3.2Zn was used and found to be a simple and rapid method to fluorescently detect the PPi released from dNTPs in a polymerase chain reaction (PCR).

Figure 4A:
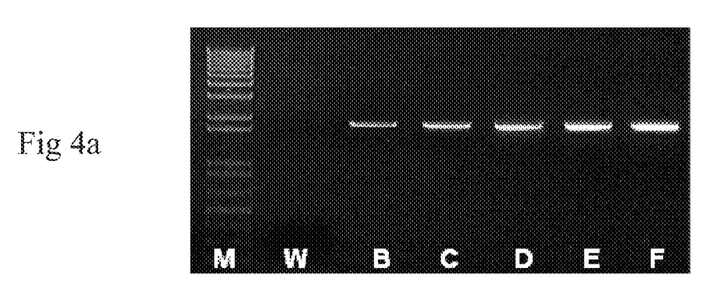
FIG. 4(a) is a photograph showing the result of gel electrophoresis of finished PCT mixtures.
Figure 4B:
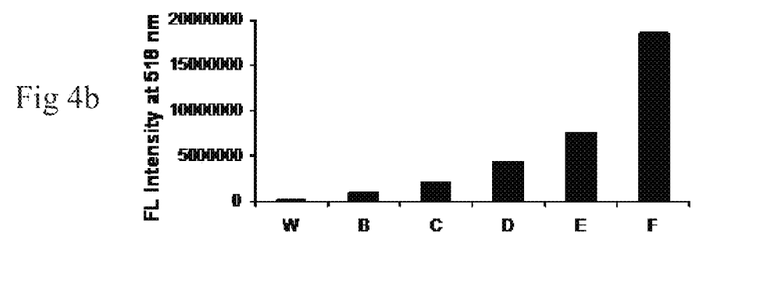
FIG. 4(b) is a schematic representation of the fluorescence intensity at 518 nanometers (nm) for finished PCT mixtures.

Gel electrophoresis of finished PCR mixtures is shown in FIG. 4(a). The gel electrophoresis revealed the production of DNA of the same molecular weight, where the band intensity was proportional to the amount of PPi released from PCR and subsequently detected by the fluorescence intensity at 518 nm, as shown in FIG. 4(b). More specifically, FIG. 4(b) shows fluorescence intensity of sensor 3.2Zn at 518 nm upon addition of the finished PCR product mixture. W: 10 µl of finished PCR product mixture performed without template DNA; 10 µl of finished PCR product mixture performed with template DNA after B: 21 cycles; C:22 cycles; D:23 cycles; E:24 cycles; F:25 cycles. M: show as DNA marker. These results illustrate that the sensor 3.2Zn provides a simple and fast way to monitor PCR process by sensor's virtue of selectivity and sensitivity.

A new ratiometric sensor based on a unique ESIPT turn-on mechanism is provided by the present invention. The two DPA-$Zn^{2+}$ groups in the sensor 3.2Zn, which were located in suitable distance, create a strong binding environment to selectively recognize PPi over structurally similar phosphate ATP and other anions. Utilization of this molecular recognition event to trigger the ESIPT results in a large fluorescent bathochromic shift (~100 nm). Large fluorescence response, in addition to its excellent selectivity toward PPi, points to that the probe molecule could be used for various biochemical and analytical applications.

Various modifications and alterations that do not depart from the scope and spirit of this invention will become apparent to those skilled in the art. This invention is not to be duly limited to the illustrative embodiments set forth herein.

What is claimed is:

1. A dinuclear zinc complex PPi sensor represented by the formula

3·2Zn having two $Zn^{2+}$ centers and a phenoxide oxygen, wherein X is selected from the group consisting of hydrogen, —COOEt, —CH=$CH_2$, —OR, and —$NR_2$, wherein R is a monovalent organic group having from 1 to about 20 carbon atoms, and wherein one of the $Zn^{2+}$ centers is bound to the phenoxide oxygen atom.

2. The sensor of claim 1, wherein X is hydrogen.

3. The sensor of claim 1, wherein the two $Zn^{2+}$ centers are separated by about 7.35 Å.

4. A method of preparing a dinuclear zinc complex PPi sensor, the method comprising the steps of:
(1) reacting 2-(2'-hydroxyphenyl)-benzoxazole (HBO) or a derivative of HBO with 1-3 hexamethylenetetramine (HMTA) via a dual-Duff reaction, to form a dialdehyde intermediate that may be represented by the formula wherein X is selected from the group consisting of hydrogen, —COOEt, —CH=CH$_2$, —OR, and —NR$_2$, and wherein R is a monovalent organic group having from 1 to about 20 carbon atoms; then
(2) combining the dialdehyde, sodium triacetoxyborohydride [NaBH(OAc)$_3$], and a bis(2-pyridylmethyl)amino compound in a reductive amination reaction, to form a compound containing two bis(2-pyridylmethyl)amino groups, said compound being represented by the formula

3 then
(3) combining the product of the reductive amination reaction with zinc nitrate Z$_n$(NO$_3$)$_2$ to form a dinuclear Zn$^{2+}$ complex, that may be represented by the formula 3·2Zn wherein one of the Zn$^{2+}$ cations is bonded to a phenol oxygen, removing the phenolic proton and turning off the luminescence from the excited state intramolecular proton transfer (ESIPT).

5. A method of detecting PPi in an aqueous, the method comprising the steps of providing an aqueous solution containing a di-nuclear Zn complex PPi sensor capable of reacting with PPi, said PPi sensor having a structure represented by the formula.

3·2Zn wherein X is selected from the group consisting of hydrogen, —COOEt, —CH=CH$_2$, —OR, and —NR$_2$, wherein R is a monovalent organic group having from 1 to about 20 carbon atoms, and wherein any PPi present in the aqueous solution will combine with said dinuclear Zn complex, thereby creating a measurable fluorescent signal.

6. A method of pyrosequencing is provided, the method comprising the steps of (1) providing a DNA template having a base at a target position and an extension primer; (2) subjecting the DNA template and extension primer to a polymerase reaction in the presence of (a) a deoxynucleotide or dideoxynucleotide, and (b) a dinuclear zinc complex PPi sensor represented by the formula 3·2Zn X is selected from the group consisting of hydrogen, —COOEt, —CH=CH$_2$, —OR, and —NR$_2$, wherein R is a monovalent organic group having from 1 to about 20 carbon atoms, wherein said nucleotide will become incorporated onto the DNA template and release PPi if the nucleotide is complementary to the base in the target position, and wherein said released PPi combines with said dinuclear zinc complex and a fluorescent emission is produced.

7. The method of claim 5, wherein a large fluorescent bathochromic shift of at least about 100 nm is generated.

8. The method of claim 5, wherein said fluorescent emission is produced with peak $\lambda_{em}$=518 nm.

9. The method of claim 6, wherein different deoxynucleotides or dideoxynucleotides are added either to separate aliquots of DNA-primer mixture or successively to the same DNA-primer mixture and subjected to the polymerase reaction to indicate which nucleotide is incorporated.

10. The method of claim 6, wherein said step of subjecting the DNA template and extension primer to a polymerase reaction takes place in aqueous droplets in an oil phase.

* * * * *